US006884798B2

(12) United States Patent
Baron et al.

(10) Patent No.: US 6,884,798 B2
(45) Date of Patent: Apr. 26, 2005

(54) FUNGICIDAL AGENT COMBINATIONS

(75) Inventors: Gerhard Baron, Leverkusen (DE); Michael Kilian, Leverkusen (DE); Frank Rosenfeldt, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 57 days.

(21) Appl. No.: 10/432,756

(22) PCT Filed: Nov. 19, 2001

(86) PCT No.: PCT/EP01/13339

§ 371 (c)(1), (2), (4) Date: May 27, 2003

(87) PCT Pub. No.: WO02/43495

PCT Pub. Date: Jun. 6, 2002

(65) Prior Publication Data

US 2004/0047928 A1 Mar. 11, 2004

(30) Foreign Application Priority Data

Dec. 1, 2000 (DE) ........................ 100 59 605

(51) Int. Cl.$^7$ ........................ A01N 43/653; A01N 65/00
(52) U.S. Cl. .................... 514/195.1; 514/383
(58) Field of Search ............................ 514/383, 195.1, 514/229.2, 256, 384, 395, 463, 467, 479, 539, 563, 567

(56) References Cited

U.S. PATENT DOCUMENTS

| | | | |
|---|---|---|---|
| 4,532,341 A | 7/1985 | Holmwood et al. | 549/559 |
| 4,626,595 A | 12/1986 | Holmwood et al. | 549/559 |
| 4,723,984 A | 2/1988 | Holmwood et al. | 71/76 |
| 4,789,672 A | 12/1988 | Holmwood et al. | 514/184 |
| 4,851,405 A | 7/1989 | Krámer et al. | 514/212 |
| 4,871,390 A | 10/1989 | Holmwood et al. | 71/92 |
| 4,897,107 A | 1/1990 | Holmwood et al. | 71/92 |
| 4,904,298 A | 2/1990 | Holmwood et al. | 71/92 |
| 4,911,746 A | 3/1990 | Holmwood et al. | 71/92 |
| 5,059,623 A | 10/1991 | Krüger et al. | 514/613 |
| 5,145,856 A | 9/1992 | Clough et al. | 514/274 |
| 5,264,440 A | 11/1993 | Clough et al. | 514/269 |
| 5,356,628 A | 10/1994 | Locke et al. | 424/405 |
| 5,368,856 A * | 11/1994 | Locke et al. | 424/761 |
| 5,395,837 A | 3/1995 | Clough et al. | 514/269 |
| 5,411,736 A | 5/1995 | Locke et al. | 424/410 |
| 5,453,531 A | 9/1995 | Seitz et al. | 560/29 |
| 5,468,747 A | 11/1995 | Clough et al. | 514/239.5 |
| 5,789,430 A | 8/1998 | Jautelat et al. | 514/272.4 |
| 5,859,039 A | 1/1999 | Jautelat et al. | 514/384 |
| 6,103,717 A | 8/2000 | Heinemann et al. | 514/229.2 |
| 6,407,233 B1 | 6/2002 | Heinemann et al. | 544/65 |

FOREIGN PATENT DOCUMENTS

| | | |
|---|---|---|
| CA | 2043733 | 12/1991 |
| EP | 0 591 674 | 4/1994 |
| WO | 97/12736 | 4/1997 |

OTHER PUBLICATIONS

The Pesticide Manual, 11$^{th}$ edition, British Crop Protection Council (month unavailable) 1997, No. 36, pp. 59–60, "azadirachtin".
Weeds, 15 (month unavailable) 1967, pp. 20–22, S.R. Colby, "Calculating Synergistic and Antagonistic Responses of Herbicide Combinations".
The Pesticide Manual, 11$^{th}$ edition, British Crop Protection Council (month unavailable) 1997, No. 678 "tebuconazole".
The Pesticide Manual, 11$^{th}$ edition, British Crop Protection Council, (month unavailable) 1997, No. 721, "triadimenol".
The Pesticide Manual, 11$^{th}$ edition, British Crop Protection Council, (month unavailable) 1997, No. 505, "myclobutanil" pp. 854–856.
The Pesticide Manual, 11$^{th}$ edition, British Crop Protection Council, (month unavailable) 1997, No. 60, "benomyl" pp. 100–102.
The Pesticide Manual, 11$^{th}$ edition, British Crop Protection Council, (month unavailable) 1997, No. 107, "carbendazim".
The Pesticide Manual, 11$^{th}$ edition, British Crop Protection Council, (month unavailable) 1997, No. 43, "azoxystrobin" pp. 70–72.
The Pesticide Manual, 11$^{th}$ edition, British Crop Protection Council, (month unavailable) 1997, No. 439, "kresoxim-methyl".
The Pesticide Manual, 11$^{th}$ edition, British Crop Protection Council, (month unavailable) 1997, No. 441, "KWG 4168–spiroxamine" p. 746–747.

* cited by examiner

Primary Examiner—S. Mark Clardy
(74) Attorney, Agent, or Firm—Richard E. L. Henderson

(57) ABSTRACT

The invention relates to novel active compound combinations of extracts from seeds of the Neem tree and the active compounds of groups (B) to (E) listed in the disclosure, that have very good fungicidal properties.

4 Claims, No Drawings

FUNGICIDAL AGENT COMBINATIONS

The present patent application has been filed under 35 U.S.C. 371 as national stage application of PCT/EP01/13339, filed Nov. 19. 2001, which was published in German as International Patent Publication WO 02/434950 on Jun. 6, 2002, which is entitled to the right of priority of German Patent Application 100 59 605.3, filed Dec. 1, 2000.

The present invention relates to novel active compound combinations which comprise, firstly, known extracts from seeds of the Neem tree and, secondly, further known fungicidally active compounds, and which are highly suitable for controlling phytopathogenic fungi.

It is already known that extracts from the seeds of the Neem tree have fungicidal properties (cf. "The Pesticide Manual", 11th. Edition, 1997, The British Crop Protection Council, No. 36 and EP-A 0 436 257). The activity of this substance is good; however, it is sometimes unsatisfactory at low application rates.

It is furthermore known that numerous azole derivatives, strobilurin derivatives and also other heterocycles can be used for controlling fungi (cf. EP-A 0 040 345, EP-A 0 281 842, EP-A 0 339 418, EP-A 0 382 375 and WO 96-16 048). However, the activity of these substances is likewise not always satisfactory at low application rates.

It has now been found that the novel active compound combinations comprising.
A) extracts from seeds of the Neem tree
and
B) an active compound from the group of the triazole derivatives, consisting of
  (1) tebuconazoles,
  (2) triadimenole,
  (3) myclobutanile and
  (4) 2-[2-(1-chlorocyclopropyl)-3-(2-chlorophenyl)-2-hydroxypropyl]-2,4dihydro [1,2,4]triazole-3-thione
or
C) an active compound from the group of the benzimidazole derivatives, consisting of
  (5) benomyl,
  (6) carbendazim and
or
D) an active compound from the group of the strobilurin derivatives, consisting of
  (7) azoxystrobin,
  (8) kresoxime methyl,
  (9) trifloxystrobin and
  (10) 3-[1-(2-[4-(2-chlorophenoxy)-5-fluoropyrimid-6-yloxy]phenyl)-1-(methoximino) methyl]-5,6-dihydro-1,4,2-dioxazine
or
(E) an active compound from the group consisting of
  (11) spiroxamine,
  (12) fenhexamide and
  (13) iprovalicarb,
have very good fungicidal properties.

Surprisingly, the fungicidal activity of the active compound combinations according to the invention is considerably higher than the sum of the activities of the individual active compounds. Thus, an unforeseeable, true synergistic effect is present, and not just an addition of activities.

In the present case, extracts from seeds of the Neem tree are to be understood as meaning all customary products which can be isolated from the seeds of the Neem tree by extraction or squeezing and which contain substantial quantities of azadirachtin. These products include azadirachtin itself.

The various extracts of seeds of the Neem tree and azadirachtin itself are already known (cf. "The Pesticide Manual" 11th. Edition, British Crop Protection Council 1997, No. 36 and also "Römpp Chemie Lexikon", 9th Edition, page 2954, Georg Thieme Verlag, Stuttgart-New York, 1991).

The fungicidally active components which are present in the active compound combinations according to the invention in addition to the extracts from the seeds of the Neem tree are likewise known. The following substances are specifically described in "The Pesticide Manual" 11th Edition, British Crop Protection Council, 1997:

| (1) tebuconazole | under No. 678, |
| (2) triadimenol | under No. 721, |
| (3) myclobutanil | under No. 505, |
| (5) benomyl | under No. 60, |
| (6) carbendazim | under No. 107, |
| (7) azoxystrobin | under No. 43, |
| (8) kresoxime methyl | under No. 439 and |
| (11) spiroxamine | under No. 441. |

The other of the abovementioned active compounds are described in the following publications:

| (4) triazole derivative | WO 96-16 048, |
| (9) trifloxystrobin | EP-A 0 460 575, |
| (10) strobilurin derivative of the formula (III) | EP-A 0 882 043. |
| (12) fenhexamide | EP-A 0 339 418 and |
| (13) iprovalicarb | EP-A 0 472 996. |

In addition to the extract from the seeds of the Neem tree, the active compound combinations according to the invention comprise at least one of the active compounds from groups (B) to (E). Additionally, they may also comprise further fungicidally active co-components.

The synergistic effect is particularly pronounced if the active compounds are present in the active compound combinations according to the invention in certain weight ratios. However, the weight ratios of the active compounds in the active compound combinations can be varied within a relatively wide range. In general,
  from 0.1 to 25 parts by weight, preferably from 0.2 to 20 parts by weight, of active compound from group (B),
  from 0.1 to 50 parts by weight, preferably from 0.2 to 40 parts by weight, of active compound from group (C),
  from 0.1 to 25 parts by weight, preferably from 0.2 to 20 parts by weight, of active compound from group (D) or
  from 1 to 60 parts by weight, preferably from 20 to 50 parts by weight, of active compound from group (E)
  are present per part by weight of extract from seeds of the Neem tree.

The active compound combinations according to the invention have very good fungicidal properties and can be used for controlling phytopathogenic fungi, such as plasmodiophoromycetes, oomycetes, chytridiomycetes, zygomycetes, ascomycetes, basidiomycetes, deuteromycetes, etc.

The active compound combinations according to the invention are particularly suitable for controlling powdery and downy mildew fungi, leaf blotch pathogens and rust, such as Sphaerotheca, Septoria and Puccinia. Moreover, they can also be used with good results against soil-borne fungi, such as Fusarium, Pythium and Rhizoctonia.

The fact that the active compound combinations are well tolerated by plants at the concentrations required for controlling plant diseases permits the treatment of above-ground parts of plants, of propagation stock and seeds, and of the soil. The active compound combinations according to the invention can be used for foliar application or else as seed dressing.

The active compound combinations according to the invention are usually employed in the form of compositions (formulations), for the preparation f which it is possible to use the extracts from seeds of the Neem tree in a commercial preparation or in the form of isolated substances and the active compounds of groups (B) to (E) either as such or in commercial preparations.

The active compound combinations according to the invention can be converted into the customary compositions (formulations), such as solutions, emulsions, suspensions, powders, foams, pastes, granules, aerosols, microencapsulations in polymeric compounds and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane, or paraffins, for example petroleum fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulfoxide, and also water. Liquefied gaseous extenders or carriers refer to those liquids which are gaseous at normal temperature and under atmospheric pressure, for example aerosol propellants, such as butane, propane, nitrogen and carbon dioxide. Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks, such as calcite, marble, pumice, sepiolite and dolomite, or else synthetic granules of inorganic and organic meals, and granules of organic materials such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignosulfite waste liquors and methylcellulose.

Tackifiers, such as carboxymethylcellulose and natural and synthetic polymers, in the form of powders, granules or latices, such as gum arabic, polyvinyl alcohol and polyvinyl acetate, or else natural phospholipids, such as cephalins and lecithins and synthetic phospholipids, can be used in the formulations. Other possible additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compounds, preferably between 0.5 and 90%.

In the formulations, the active compound combinations according to the invention can be present as a mixture with other known active compounds, such as fungicides, insecticides, acaricides and herbicides, and as mixtures with fertilizers or plant growth regulators.

The active compound combinations can be employed as such, in the form of their formulations or of the use forms prepared therefrom, such as ready-to-use solutions, emulsifiable concentrates, emulsions, suspensions, wettable powders, soluble powders, granules and shaped articles. The application is carried out in a customary manner, for example by watering, spraying, atomizing, scattering, spreading, dry dressing, wet dressing, liquid dressing, slurry treatment of seeds, incrustation, implantation or injection.

When using the active compound combinations according to the invention, the application rates can be varied within a relatively wide range, depending on the type of application. In the treatment of parts of plants, the application rates of active compound combination are generally between 20 and 5000 g/ha, preferably between 30 and 1000 g/ha. In the treatment of seeds, the application rates of active compound combination are generally between 0.001 and 50 g/kilogram of seed, preferably between 0.01 a 10 g/kilogram of seed. In the treatment of the soil, the application rates of active compound combination are generally between 20 and 5000 g/ha, preferably between 30 and 1000 g/ha.

The good fungicidal activity of the active compound combinations according to the invention is demonstrated by the examples below. Whereas the individual active compounds have weaknesses in the fungicidal activity, the combinations have an activity which exceeds a simple addition of activities.

A synergistic effect of fungicides is therefore always present when the fungicidal activity of the active compound combinations exceeds the total of the activities of the active compounds when applied individually.

The expected activity for a given combination of two active compounds can be calculated according to S. R. Colby, ("Calculating Synergistic and Antagonistic Responses of Herbicide Combinations", Weeds 15 (1967), 20–22), as follows:

If

X is the efficacy when applying the active compound A at an application rate of m g/ha, Y is the efficacy when applying the active compound B at an application rate of n g/ha and E is the efficacy when applying the active compounds A and B at application rates of m and n g/ha, then $$E = X + Y - \frac{X \cdot Y}{100}$$

Here, the efficacy is determined in %. 0% means an efficacy which corresponds to that of the control, whereas an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the formula given above.

The invention is illustrated by the following examples:

EXAMPLES

Sphaerotheca Test Roses/Curative

To produce a suitable preparation of active compound, a commercial formulation of active compound or active compound combination is mixed with water until the desired concentration is reached.

To test for curative activity, roses infected with *Sphaerotheca pannosa* are sprayed three times, at intervals of in each case 7 days, with the preparation of active compound at the stated application rate. The plants are placed in a greenhouse at temperatures between 15° C. and 23° C. and a relative atmospheric humidity of about 70%.

Evaluation is carried out 10 or 20 days after the third treatment. 0% means an efficacy which corresponds to that of the control, whereas an efficacy of 100% means that no infection is observed.

Active compounds, application rates and test results are shown in the table below.

TABLE 1

Sphaerotheca test Roses/curative

| Active compound | Application rate of active compound in g/ha | Efficacy in % 10 days after the third treatment | Efficacy in % 20 days after the third treatment |
|---|---|---|---|
| Known: | | | |
| Neem extract*) | 40 | 10.3 | 3.6 |
| tebuconazoles | 100 | 28.6 | 26.6 |
| According | | | |

TABLE 1-continued

Sphaerotheca test Roses/curative

| Active compound | Application rate of active compound in g/ha | Efficacy in % 10 days after the third treatment | | Efficacy in % 20 days after the third treatment | |
|---|---|---|---|---|---|
| | | found | calc.) | found | calc.) |
| to the invention: | | | | | |
| Neem-Extrakt* + Tebuconazoles | 40 + 100 | 47.2 | 36.0 | 44.3 | 29.2 |

*)The Neem tree seed extract used is commercially available under the name Neem-Azal ® (from Trifolio).
**)found = activity found
calc. = activity calculated using Colby's formula

What is claimed is:

1. A fungicidal composition comprising an active compound combination comprising
   (A) extracts from seeds of the Neem tree, and
   (B) tebuconazole,
   and one or more extenders and/or surfactants.

2. A composition as claimed in claim 1 wherein the weight ratio of the extract from seeds of the Neem tree to tebuconazole is from 1:0.1 to 1:25.

3. A method for controlling fungi comprising applying an effective amount of an active compound combination as claimed in claim 1 to the fungi and/or their habitats.

4. A process for preparing a fungicidal composition comprising mixing an active compound combination as claimed in claim 1 with one or more extenders and/or surfactants.

* * * * *